United States Patent [19]
Daikuzono

[11] Patent Number: 5,948,008
[45] Date of Patent: *Sep. 7, 1999

[54] APPARATUS FOR TREATMENT OF LUMBAR DISC HERNIATION

[75] Inventor: Norio Daikuzono, Cincinnati, Ohio

[73] Assignee: S.L.T. Japan Co., Ltd., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/580,243

[22] Filed: Dec. 28, 1995

[51] Int. Cl.⁶ .................................................. A61B 17/36
[52] U.S. Cl. .......................... 607/89; 607/116; 607/117; 606/15; 606/16; 606/167; 606/180
[58] Field of Search .................................. 606/10–13, 14, 606/15, 16, 3, 180, 167; 607/116, 117, 89; 604/20–22

[56] References Cited

U.S. PATENT DOCUMENTS

| | | | |
|---|---|---|---|
| 4,950,267 | 8/1990 | Ishihara et al. | 606/12 |
| 5,061,266 | 10/1991 | Hakky | 606/15 |
| 5,203,770 | 4/1993 | Wigness et al. | 604/51 |
| 5,209,748 | 5/1993 | Daikuzono | 606/15 |
| 5,222,953 | 6/1993 | Dowlatshahi | 606/15 |
| 5,242,439 | 9/1993 | Larsen et al. | 606/15 |
| 5,290,276 | 3/1994 | Sewell, Jr. | 606/15 |
| 5,320,617 | 6/1994 | Leach | 606/15 |
| 5,437,661 | 8/1995 | Rieser | 606/16 |

OTHER PUBLICATIONS

"Percutaneous Laser Disc Decompression," *Spine*, vol. 17, No. 8, Aug. 1992.
"Fall of Intradiscal Pressure with Laser Ablation," *Spine*, vol. 7, No. 1, Jan. 1993.
"Radiological Considerations: Percutaneous Laser Disc Decompression," *Journal of Clinical Laser Medicine & Surgery*, vol. 11, No. 5, 1993.
"The System and Procedures of Percutaneous Intradiscal Laser Nucleotomy," *Spine*, vol. 15, No. 11, 1990.

*Primary Examiner*—Linda C.M. Dvorak
*Assistant Examiner*—Rosiland Kearney
*Attorney, Agent, or Firm*—McDermott, Will & Emery

[57] ABSTRACT

An apparatus, for laser irradiating and vaporizing the nucleus pulposus of the lumbar intervertebral disc, comprises a hollow needle member; an optical fiber for transmitting a laser light; a lead for detecting the temperature of the nucleus pulposus. The optical fiber and the temperature detecting lead are disposed such that they pass through the needle member adjacent the nucleus pulposus. Insertion is confirmed by ultrasonic diagnosis.

5 Claims, 6 Drawing Sheets

APPARATUS FOR TREATMENT OF LUMBAR DISC HERNIATION

DETAILED DESCRIPTION OF THE INVENTION

1. Field of the Invention

The present invention relates to an apparatus for treatment of lumbar disc herniation.

2. Prior Art

Lumbar intervertebral discs are disc-shaped tissue located between the vertebrae and comprise a gelatinous nucleus pulposus which is centrally located and is rich in water content and a peripheral annulus fibrosus which consists of fibrous cartilage.

Lumbar intervertebral disc herniation is a disease in which the nucleus pulposus is herniated rearward to press the spinal core or the nerve root due to deformation or damages of annulus fibrosus so that nerve symptom is exhibited.

Treatment of the lumbar intervertebral disc herniation includes treatment by injecting steroid into intervertebral discs (SIDT) or surgical operation for removing the herniated nucleus pulposus per se (LOVE method). Recently, for relatively light cases, treatments including (1) surgery for removing the annulus fibrosus by suction, (2) surgery for removing the herniated tissue using tweezers under a microscope and (3) laser irradiation method have been tried to enhance the effectiveness of treatment.

After Percutaneous Laser Disc Decompression (PLDD) surgery in which reduction in pressure on the annulus fibrosus was examined by Choy and Ascher, its effectiveness was confirmed. This PLDD method has advantages in that the surgical operation is simple, the operation invasion is light, and the period of time for which the patient must be in hospital bed is very short.

The treatment apparatus includes a needle having an outer tube and inner tube, which are coaxially disposed and an optical fiber which is inserted into the inner tube. The apparatus is inserted into the nucleus pulposus. Vaporization of the nucleus pulposus is conducted by irradiating it with a laser light transmitted through the optical fiber. Fresh air is pumped under pressure via a space between the inner tube and the optical fiber for externally discharging the air with the vaporized material through a space between the outer and inner tubes.

However the needle has a large diameter since it is double lumen tube to provide both a fresh air introducing space and vaporized material discharging space. Accordingly, the surgery gives a great pain to the patients during insertion.

On the other hand since the degree of the vaporization of the nucleus pulposus can not be visually observed, the laser light irradiation period of time and the laser light output can not be controlled and the surgery operation should be empirically conducted, resulting in a limited enhancement in effectiveness of the operation.

SUMMARY OF THE INVENTION

Therefore, it is an object of the present invention to decrease the outer diameter of the needle and to make it possible to properly conduct an operation.

In order to accomplish the above-mentioned object, the present invention provides an apparatus for treating the lumbar intervertebral disc herniation in the waist by irradiating the nucleus pulposus of the lumbar intervertebral disc with a laser light for vaporizing the nucleus pulposus; characterized in that said apparatus comprises a hollow needle member which is percutaneously inserted into the nucleus pulposus of the lumbar intervertebral disc; an optical fiber for transmitting a laser light from a laser light generator to emit the laser light from the front end thereof; a lead for detecting the temperature of the nucleus pulposus; and in that said optical fiber and said temperature detecting lead are disposed in such a manner that they pass through said needle member and can be adjacent to the nucleus pulposus.

Said optical fiber and the temperature detecting lead may be disposed in such a manner that they are integrally held by a holder and pass through said needle member and can be adjacent to the nucleus pulposus.

The apparatus may further include a knob which is provided at the rear end of said needle member and is held by fingers; a holder which integrally holds said optical fiber and the temperature detecting lead at the middle portion thereof; and a stop means for defining an insertion limit of said optical fiber and the temperature detecting lead when they are inserted into said needle member while they are integrally held by said holder. Said optical fiber may be positioned in said insertion limit position in such a manner that it projects beyond the front end of said needle member.

Said knob may be preferably rigid and is formed at the rear end thereof with a receiving hole communicated with a through-hole of said needle member, the middle portion of said optical fiber being integral with a rigid grip member, said grip member being integral with said holder, the front end portion of said grip member being able to be inserted into and secured to said receptacle hole.

Said apparatus may further include an ultrasonic diagnosis apparatus which forms an ultrasonic image of the lumbar intervertebral disc area and in which said needle member is formed on its outer surface with peripheral indication marks which strongly reflect the ultrasonic waves.

Said apparatus may further include a drill member having a sharp front end, which can be inserted into said needle from the rear end thereof, insertion of the drill member and the needle member into the tissue is conducted while the drill member passes through the needle member and projects beyond the front end thereof.

BRIEF DESCRIPTION OF THE INVENTION

DESCRIPTION OF THE PREFERRED EMBODIMENTS

Now, a preferred embodiment of the present invention will be described with reference to drawings.

Figure 1:
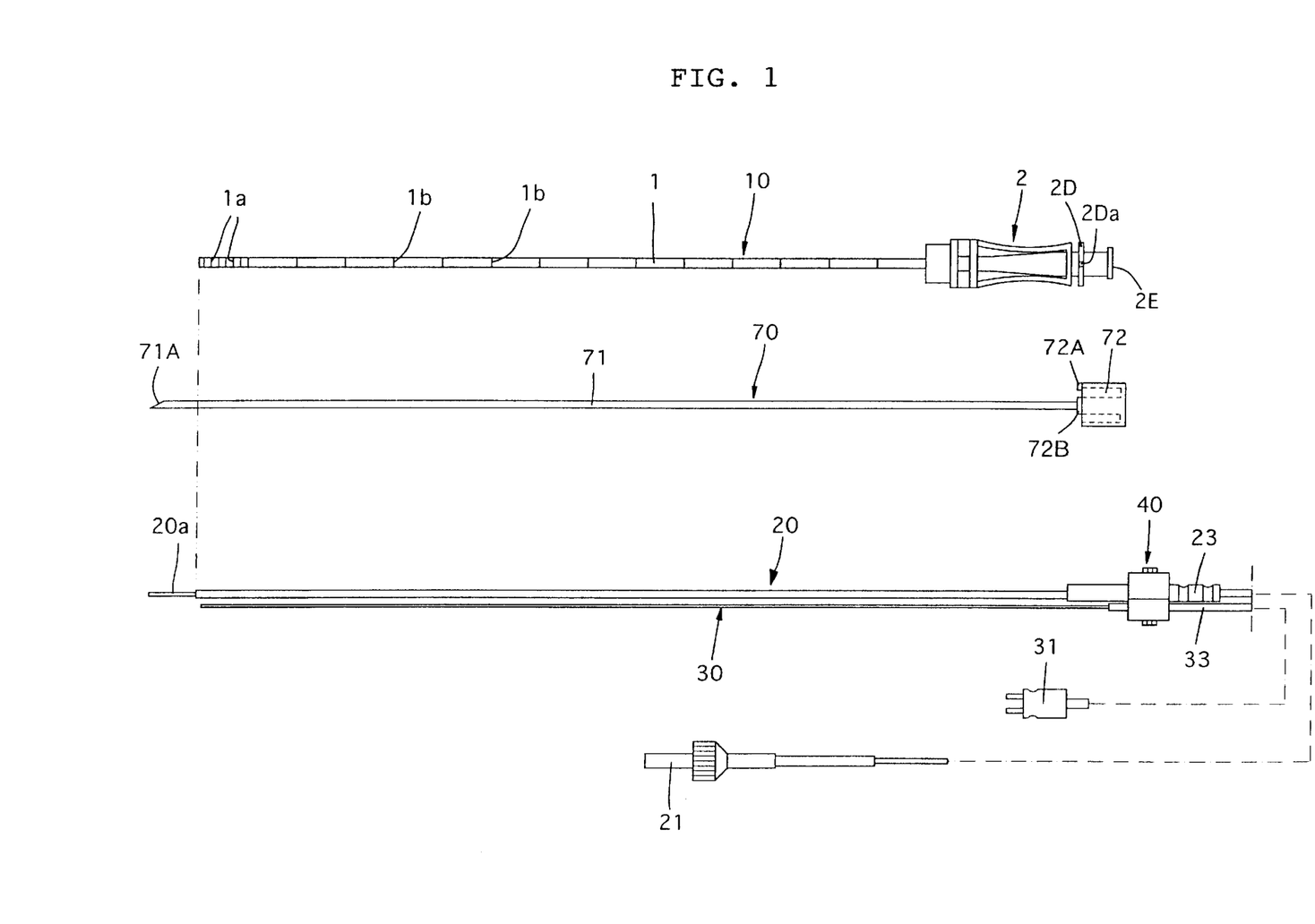
FIG. 1 is a front view showing the whole of main components of the apparatus.

FIG. 1 shows the whole of the main components of a treating apparatus.

A reference numeral 10 denotes a hollow needle member which is inserted into the nucleus pulposus of the intervertebral disc from the outside of a body. The main body of the needle 1 is made a very fine stainless steel tube having a diameter of, for example, 1 mm. The needle main body 1 is secured to the front end of a knob 2 which is a plastic molding. Insertion of the needle main body 1 into the nucleus pulposus together with a drill member 70 is conducted while an surgical operator holds the knob 2 between his or her thumb and middle finger of the right hand and holds the rear end of a drill member 70 with his or her pointing finger.

An optical fiber 20 transmits the laser light from a laser light generator to emit it from its front end. A lead 30 is provided for detecting the temperature of the nucleus pulposus. The optical fiber 20 and the temperature detecting lead 30 are integrally held by a holder 40 in their intermediate position. The optical fiber 20 is optically linked with a laser light generator 22 through a light emitting terminal 21 (refer to FIG. 5). The temperature detecting lead 30 is connected with a thermometer 32 through a terminal 31 (refer to FIG. 5).

The needle main body 1 is formed at its front or distal end with annular small recesses 1a which are spaced in a longitudinal direction thereof in order to prevent the needle 1 from escaping while the needle is inserted into the nucleus pulposus. The needle main body 1 is formed on its outer periphery with spaced indication marks 1b made of a material which strongly reflects ultrasonic waves therefrom.

Figure 2:
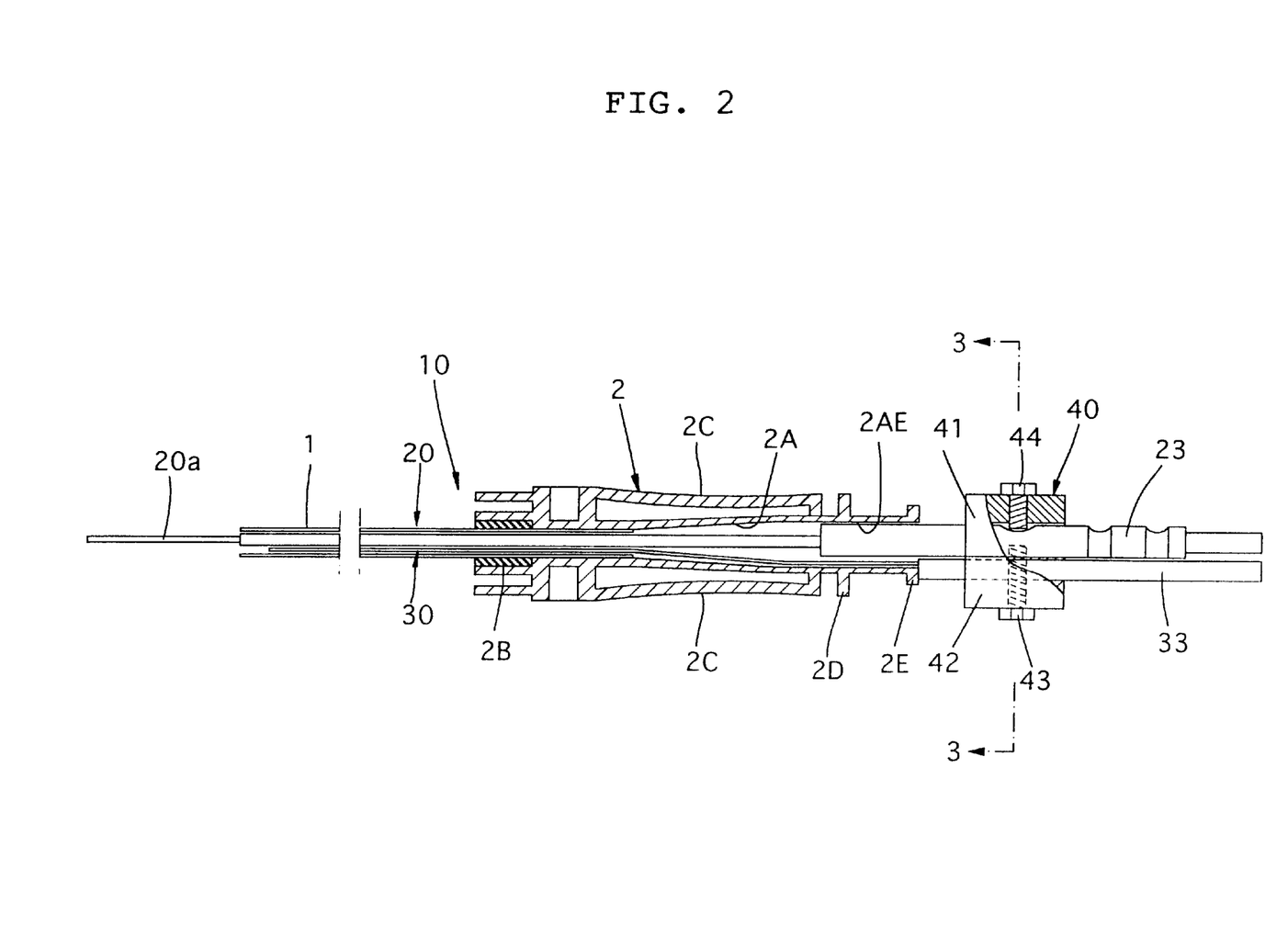
FIG. 2 is a front and partly cutaway view showing the assembly of the main components.
Figure 3:
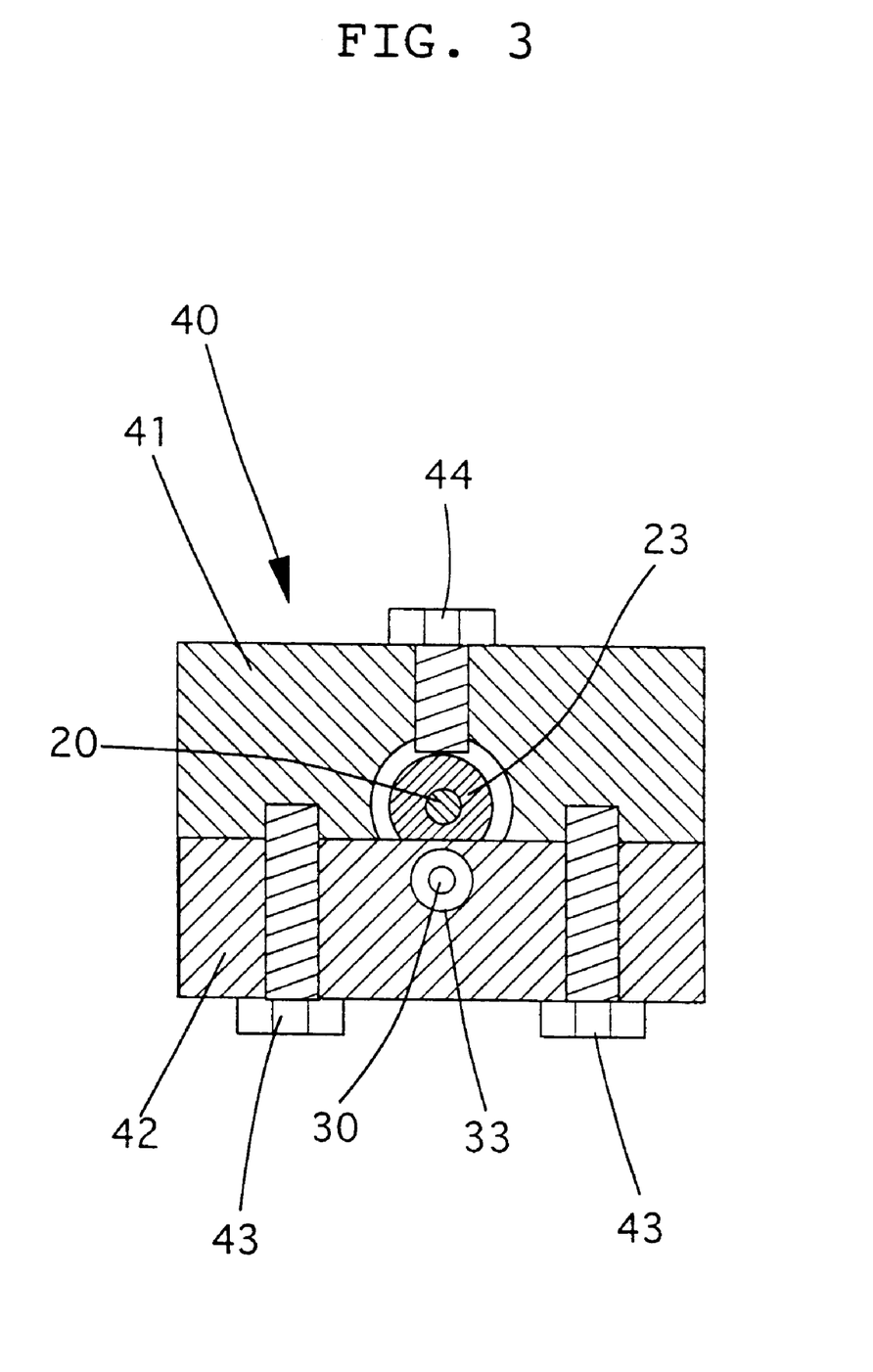
FIG. 3 is an enlarged view taken along the line 3—3 in FIG. 2.

FIGS. 2 and 3 show the relation among the needle member 10, the optical fiber 20 and the temperature detecting lead 30. The needle 1 is inserted at its rear of proximate end into an insertion hole 2A of the knob 2 and is adhesively secured thereto with an adhesive 2B. The knob 2 is substantially box-shaped in its intermediate position and has a gradual concave curved faces on the both sides thereof. The insertion hole 2A is tapered from intermediate position toward a receiving hole 2AE so that it has a smaller diameter at the front end thereof and a larger diameter at the rear end thereof. The knob 2 is formed with a flange 2D which projects from the rear portion thereof and is also formed with a smaller flange 2E at the rear end thereof. The flange 2D is formed with an engaging step 2Da on a periphery thereof in one position thereof.

The optical fiber 20 is gripped at the intermediate portion with a grip member 23 of a rigid column which is made of aluminum and is partially cut away in a longitudinal direction so that the fiber 20 is integral with the grip member 23, which is in turn integral with a holder 40. The temperature detecting lead 30 is covered with a protective tube 33 made of flexible plastics excepting its distal end portion thereof. The lead 30 is inserted into a second holder block 42 in a position slightly rear of the front end of the protective tube 33 and is secured to the block 42 with an adhesive (not shown). The holder 40 comprises a first and second holder blocks 41 and 42, which are secured to each other with a screw 43. In order to secure the grip member 40 to the holder 23, a set screw 44 is screwed through the first holder block 41 to firmly secure the outer peripheral recess of the grip member 23.

Prior to insertion of the optical fiber 20 and the temperature detecting lead 30 into the needle main body 1 of the needle member 10, it is necessary to insert the needle main body into the nucleus pulposus. Some needle main body 1 of the needle member 10 may be hollow and have a small wall thickness. Although it may be envisaged that the needle 1 may be obliquely cut at the front end thereof to make the insertion easier, there is a risk that the needle may be broken at the front end thereof on its insertion. If the tissue enters into the needle main body 1 in the course of insertion, the pierced tissue would hinder the subsequent insertion of the optical fiber 20 and the temperature detecting lead 30 to make it more difficult to do so.

Figure 4:
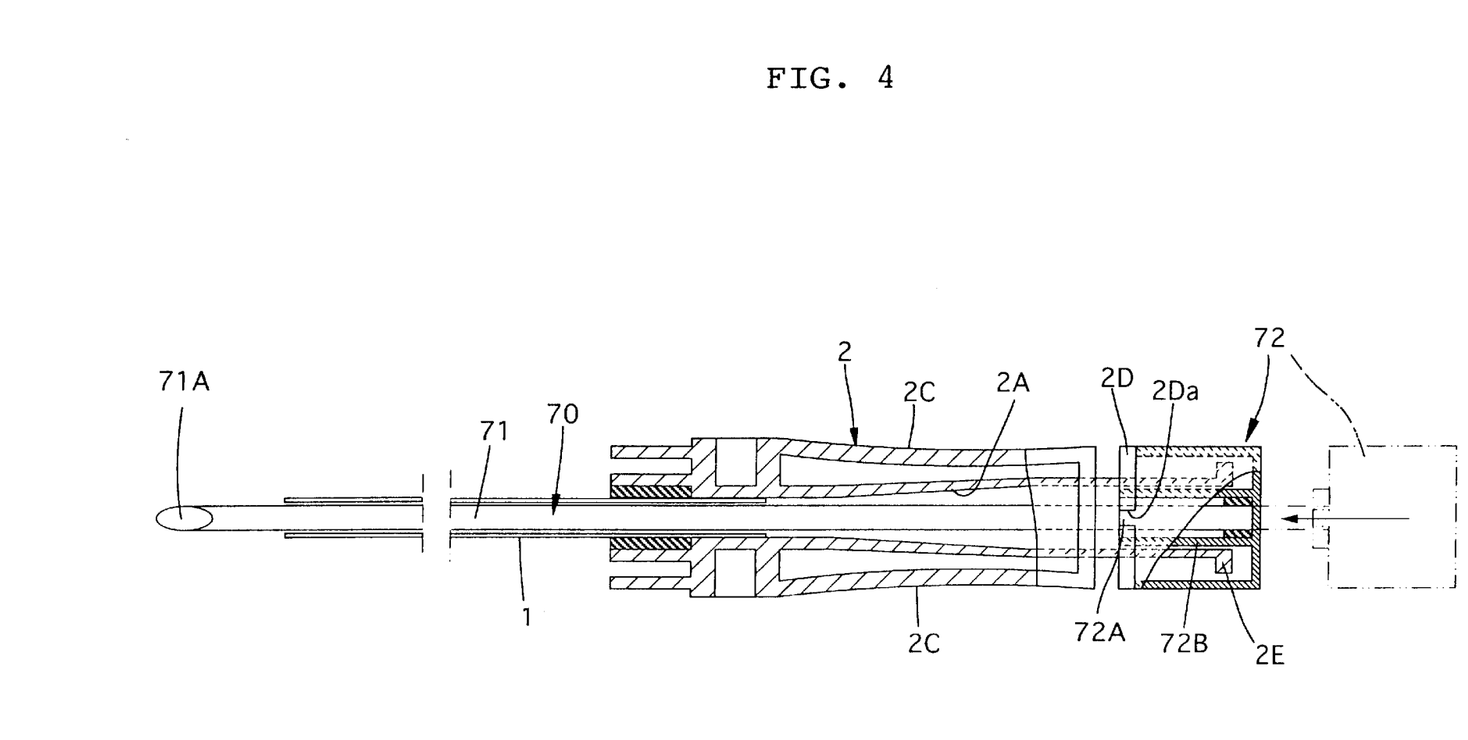
FIG. 4 is a front and partly cutaway view showing that a drill member is inserted into a needle member.

Therefore, a drill member 70 which is illustrated in detail in FIG. 4 is provided together with the needle member 10. The drill member 70 has a drill wire 71 made of stainless steel wire and a depressing member 72 made of plastic molding, which is secured to the rear end of the drill wire 71. The drill wire 71 is obliquely cut at the front or distal end thereof to provide a cut face 71A.

The depressing member 72 is formed at the central portion with a tubular recess 72B into which the rear end portion of the drill wire 71 is adapted and is secured with an adhesive (not shown). The tubular recess 72B has an outer diameter which is slightly smaller than the inner diameter of the receiving hole 2AE. The depressing member 72 is formed on the front end side in a position along the outer periphery thereof with an engaging projection 72A which projects toward the front end side. This projection 72A is adapted to be engaged with the above-mentioned engaging step 20a.

Figure 5:
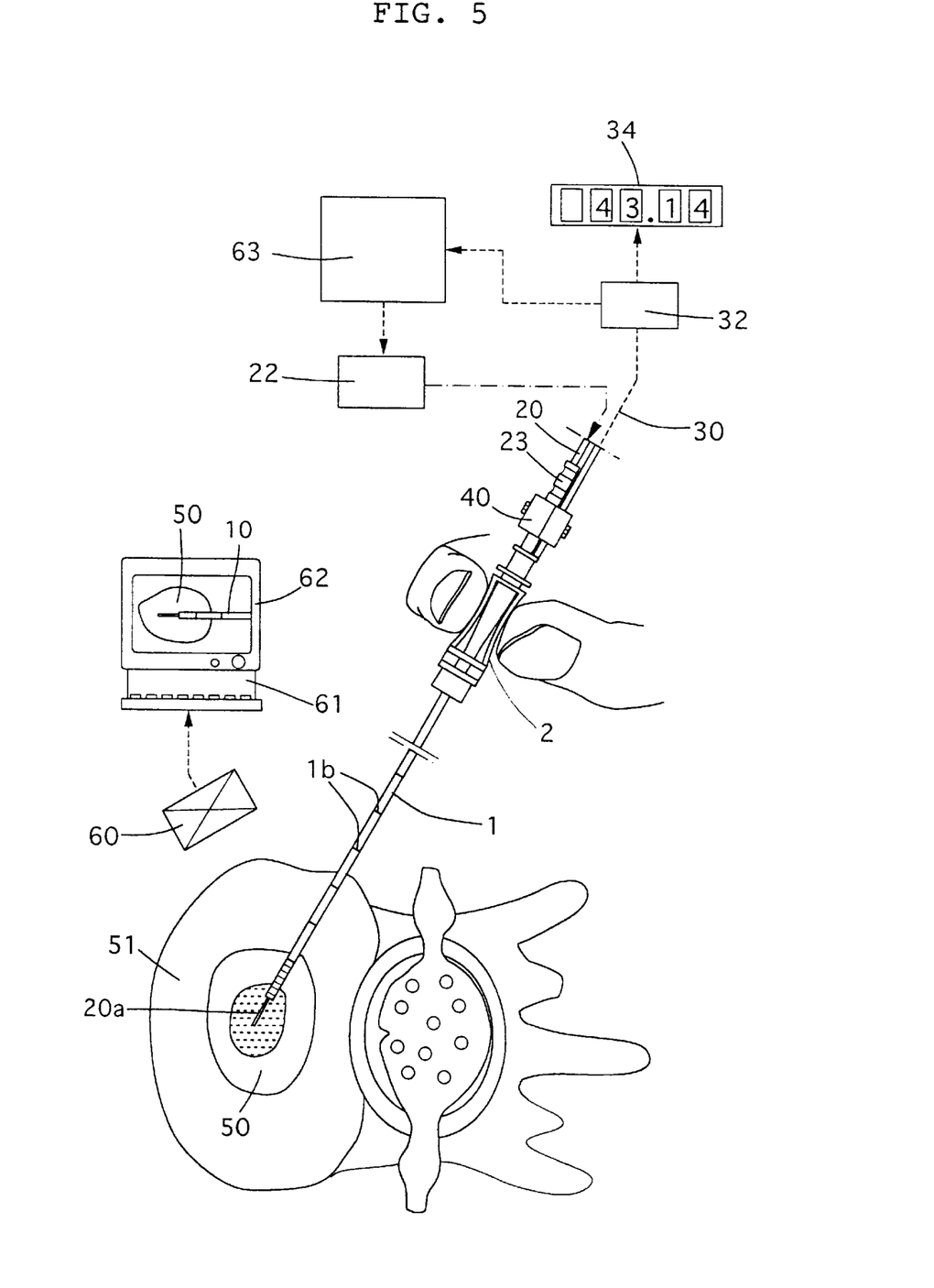
FIG. 5 is an explanatory view showing the whole of the apparatus.
Figure 6:
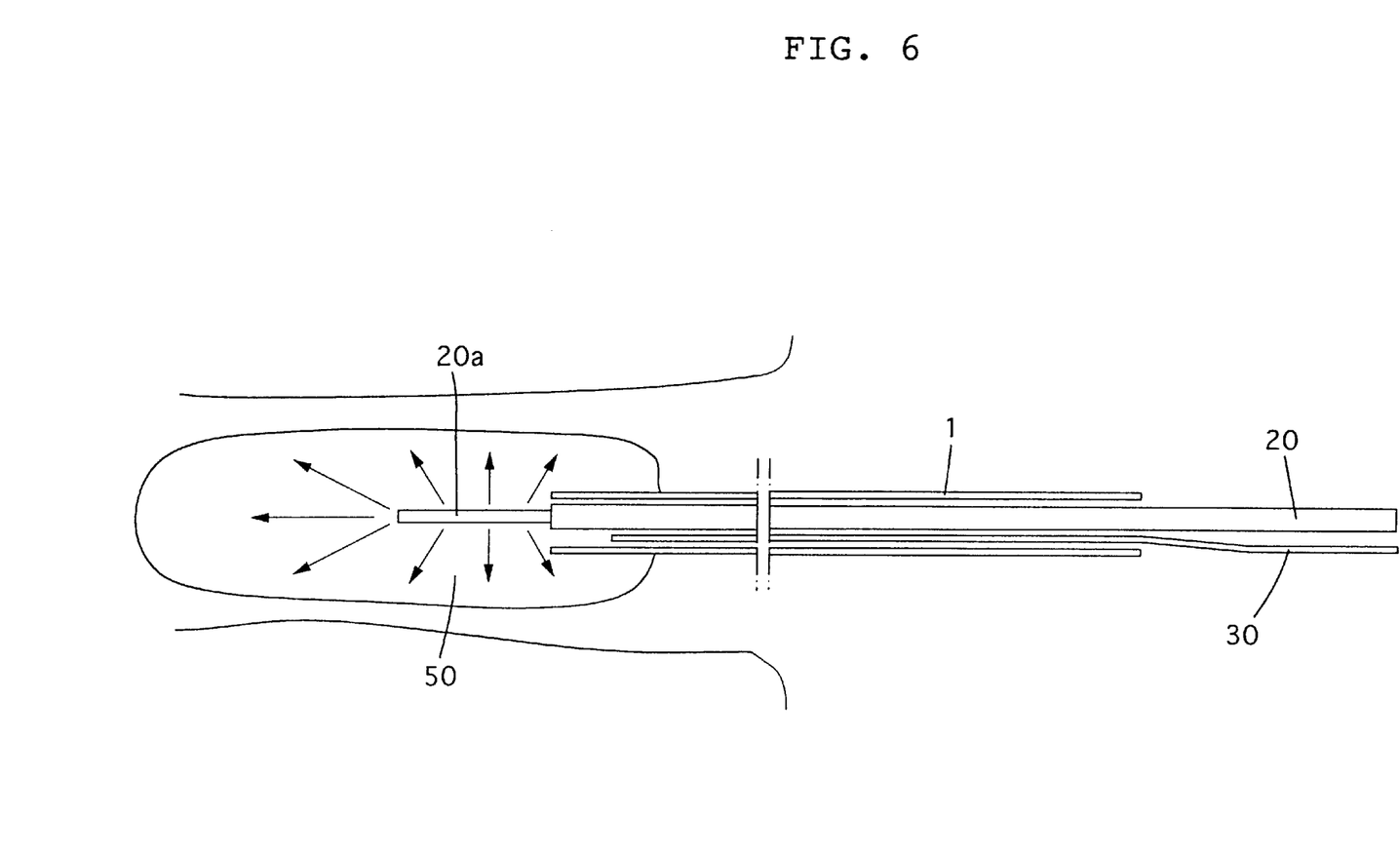
FIG. 6 is an explanatory view showing the irradiation of a intervertebral disc with a laser light.

FIGS. 5 and 6 show the whole of the treating apparatus and the insertion into the lumbar intervertebral disc, respectively.

The apparatus will be explained together with the treatment surgical operation procedure. The target lumbar intervertebral discs is firstly observed by MRI and the like. Both the needle member 10 and the drill member 70 are percutaneously inserted into the nucleus pulposus while the drill member 70 is inserted into the needle member 10 as shown in FIG. 1. A reference numeral 51 denotes the annulus fibrosus.

Specifically, the drill wire 71 is inserted into the needle main body 1 via the knob 2 while the depressing member 72 of the drill member 70 is gripped with fingers as shown in FIG. 5. Positioning of the needle member 10 and the drill member 70 in a peripheral direction is accomplished by inserting the drill wire 71 into the needle member 10 after aligning the engaging projection 72A with the above-mentioned engaging step 2Da peripheral direction (FIG. 1 shows that the drill member 70 is offset by 90 degrees around the center axis thereof with respect to the needle member 10) since the engaging projection 72A enters the engaging step 2Da to engage therewith. Simultaneously with this, the front end face of the outer peripheral portion of the depressing member 72 will abut to the flange 2D so that positioning in a longitudinal direction is accomplished. At this insertion limit, the front end of the drill wire 71 projects beyond the front end of the needle main body 1 as shown in FIG. 4.

Under this condition, both drill member 70 and the needle member 10 are percutaneously inserted into the nucleus pulposus of the lumbar intervertebral disc while the both sides 2c of the knob 2 are held by the thumb and middle finger of the right hand of the operator and the rear end of the drill member 70 is depressed by the pointing finger as mentioned above.

On insertion of the needle main body 1, no slippage of the fingers occurs since the both sides 2c of the knob 2 is concavely curved. Insertion of the needle member 10 is conducted while observing an ultrasonic image displayed by an ultrasonic diagnosis apparatus. In other words, while an ultrasonic probe 60 is brought into abutment on the body surface, the image processing is conducted by an image processor 61 based upon the resultant signal so that an image of the lumbar intervertebral disc is displayed on a CRT display 62. Since the ultrasonic waves are reflected by the needle main body 1 and more greatly reflected by the indication marks 1b, the operator can determine how deeply the needle main body 1 is inserted into the nucleus pulposus 50 by viewing the displayed image.

Subsequently, only the drill member 70 is removed to leave the needle member 10 within the body. Then, the optical fiber 20 and the temperature detecting lead 30 are inserted into the needle main body 1 via the insertion hole 2A from the rear of the knob 2 while holding the holder 40. Insertion is conducted until the front end face of the protective tube 33 will abut to the rear end face of the small flange 2E. Accordingly, in the present embodiment, the front end face of the protective tube 33 and the rear end face of the small flange 2E of the knob 2 constitute a stop which defines an insertion limit in accordance with the present invention.

In association of the insertion, the rigid grip member 23 is adapted into a receiving hole 2AE of the knob 2 having a rigidity, resulting in that the optical fiber 20 and the temperature detecting lead 30 are stably linked with the needle member 10. A bare portion of the temperature detecting lead 30 is inserted into the insertion hole 2A of the knob 2 via the cut away portion of the grip member 23.

When the fiber 20 and the lead 30 are reached at the insertion limit as shown in FIG. 2, the optical fiber 20 having an core 20a which is exposed by cutting away the front end portion of the clad is set to such a positional relation that only the core 20a projects beyond the front end face of the needle member 1. The front end face of the temperature detecting lead 30 is set to such a positional relation that it is slightly rear of the front end face of the needle member 1.

Under such a condition, irradiation with laser light is conducted. The laser light is preferably Nd:YAG or Ho:YAG laser since it is used for vaporizing the nucleus pulposus 50. When the nucleus pulposus 50 is irradiated with the laser light, vaporization of the nucleus pulposus 50 occurs. If vaporization is continued, an increase in pressure in association with the vaporization is found and some of the patient may feel heat and pain in the waist. If the optical fiber 20 and the temperature detecting lead 30 are removed from the needle member 1 via the holder 40, the vaporization pressure is discharged so that the patient is released from the heat and pain in the waist. In this case, occurrence of vaporization can be confirmed by smelling a smell of burnt nucleus pulposus 50 and viewing the deposition of carbide on the surface of the core 20a at the front end of the optical fiber 20.

After completion of the temporary removing operation, the optical fiber 20 and the temperature lead 30 are inserted into the needle member 1 again to conduct laser light irradiation. This operation is repeated two or three times. In the course of the laser light irradiation, the temperature which is detected by the lead 30 is displayed on an appropriate temperature indicator 34 via the thermometer 30. Accordingly, the laser light output and irradiation period of time is controlled based upon the temperature indicated by the temperature indicator 34. In this case, the laser light generator 22 can be controlled in such a manner that a signal from the thermometer 32 is fed to a laser light irradiation control 63 for tracing a preset pattern (correlation between the laser light output, irradiation period of time, temperature, etc.).

Vaporization of the nucleus pulposus 50 will decrease the pressure of the nucleus pulposus 50, which provides fast curing effect.

TREATMENT EXAMPLE

Investigation on 60 patients shows that the efficiency rate was 96%. This result means that this efficiency rate is very high in comparison with the efficiency rate of about 80% of the conventional PLDD treatment.

In accordance with the present invention, the outer diameter of the needle can be made not higher than 2 mm, specifically about 1 mm. Therefore, insertion is easy and burdens upon the patients become less. Proper surgical operation can be conducted by controlling the laser light irradiation based upon the detected temperature. Various advantages are provided by the present invention.

What is claimed is:

1. An apparatus for treating a herniation in a lumbar intervertebral disc comprising a nucleus pulposus by irradiating the nucleus pulposus with a laser light for vaporizing the nucleus pulposus, which apparatus comprises:

a hollow needle member, having a first end and a second end, and comprising a stopping element which is adapted to be percutaneously inserted into the nucleus pulposus of the lumbar intervertebral disc;

a drill member having a sharp front end and a depressing member at a rear end and adapted for insertion into said needle from the second end thereof, such that with the drill member being held at an insertion limit position in a longitudinal direction within the needle member by abutment of the depressing member and the stopping member, the drill member projects beyond the first end of the needle member, whereby the needle member, together with the drill member, is inserted at the same time into the nucleus pulposus of the lumbar intervertebral disc;

an optical fiber for transmitting a laser light from a laser light generator to emit the laser light from an end thereof;

a temperature detecting lead for detecting the temperature of the nucleus pulposus; wherein, said optical fiber and said temperature detecting lead are adapted for insertion within the needle member and can pass through said needle member and be positioned adjacent to the nucleus pulposus; whereby, in use, insertion of the needle member together with the drill member into the nucleus pulposus of the lumbar intervertebral disc is followed by withdrawal of the drill member from the needle member and insertion of the optical fiber within the needle member for vaporization of the nucleus pulposus.

2. An apparatus according to claim 1 which apparatus further includes an ultrasonic diagnosis apparatus which forms an ultrasonic image of a lumbar intervertebral disc area and in which said needle member comprises, on its outer surface, peripheral indication marks comprising a material which strongly reflect the ultrasonic waves.

3. An apparatus for treating a herniation in a lumbar intervertebral disc comprising a nucleus pulposus by irradiating the nucleus pulposus with a laser light for vaporizing the nucleus pulposus, which apparatus comprises:

a hollow needle member, having a first end and a second end, and comprising a stopping element which is adapted to be percutaneously inserted into the nucleus pulposus of the lumbar intervertebral disc;

a drill member having a sharp front end and a depressing member at a rear end and adapted for insertion into said needle from the second end thereof, such that with the drill member being held at an insertion limit position in a longitudinal direction within the needle member, the drill member projects beyond the first end of the needle member by abutment of the depressing member and the stopping member, whereby the needle member, together with the drill member, is inserted at the same time into the nucleus pulposus of the lumbar intervertebral disc;

an optical fiber for transmitting a laser light from a laser light generator to emit the laser light from an end thereof;

a lead for detecting the temperature of the nucleus pulposus; wherein said optical fiber and the temperature detecting lead are integrally held by a holder and adapted to pass through said needle member to be positioned adjacent to the nucleus pulposus.

4. An apparatus for treating a herniation in a lumbar intervertebral disc comprising a nucleus pulposus by irradiating the nucleus pulposus with a laser light for vaporizing the nucleus pulposus, which apparatus comprises:

a hollow needle member, having a first end and a second end, and comprising a stopping element which is adapted to be percutaneously inserted into the nucleus pulposus of the lumbar intervertebral disc;

a drill member having a sharp front end and a depressing member at a rear end and adapted for insertion into said needle from the second end thereof, such that with the drill member being held at an insertion limit position in a longitudinal direction within the needle member, the drill member projects beyond the first end of the needle member by abutment of the depressing member and the stopping member, whereby the needle member, together with the drill member, is inserted at the same time into the nucleus pulposus of the lumbar intervertebral disc;

an optical fiber for transmitting a laser light from a laser light generator to emit the laser light from a first end thereof; and a lead for detecting the temperature of the nucleus pulposus;

a knob which is provided at a second end of said needle member and is adapted to be held by fingers;

a holder which integrally holds said optical fiber and the temperature detecting lead at a middle portion thereof;

a stop means for defining an insertion limit position of said optical fiber and the temperature detecting lead when they are inserted into said needle member while they are integrally held by said holder; wherein said optical fiber is positioned in said insertion limit position in such a manner that it projects beyond the first end of said needle member.

5. An apparatus according to claim 4 in which said knob is rigid and is formed at an end thereof with a receiving hole communicating with a through-hole of said needle member, a middle portion of said optical fiber being integral with a rigid grip member, said grip member being integral with said holder, one end portion of said grip member insertable into and securable to said receiving hole.

* * * * *